United States Patent
Fuimaono et al.

(10) Patent No.: US 6,371,955 B1
(45) Date of Patent: Apr. 16, 2002

(54) ATRIAL BRANDING IRON CATHETER AND A METHOD FOR TREATING ATRIAL FIBRILLATION

(75) Inventors: Kristine B. Fuimaono, Covina, CA (US); Michel Haissaguerre, Talence (FR)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/370,605

(22) Filed: Aug. 10, 1999

(51) Int. Cl.[7] ................................................ A61B 18/18
(52) U.S. Cl. ............................ 606/41; 606/48; 606/29; 607/122; 607/116
(58) Field of Search .............................. 606/34, 39, 47, 606/48, 49, 50, 29–32, 40–42; 607/100, 101, 102, 115, 116, 119, 122; 600/374

(56) References Cited

U.S. PATENT DOCUMENTS

| | | | |
|---|---|---|---|
| 4,984,581 A | | 1/1991 | Stice |
| 5,055,109 A | * | 10/1991 | Gould .......................... 604/95 |
| 5,125,895 A | * | 6/1992 | Buchbinder .................. 604/95 |
| 5,327,905 A | * | 7/1994 | Avitall ......................... 606/45 |
| 5,383,923 A | | 1/1995 | Webster, Jr. |
| 5,487,385 A | | 1/1996 | Avitall |
| 5,545,200 A | | 8/1996 | West et al. .................. 607/122 |
| 5,643,251 A | | 7/1997 | Hillsman et al. ............... 606/7 |
| 5,700,262 A | * | 12/1997 | Acosta ......................... 606/48 |
| 5,800,428 A | | 9/1998 | Nelson et al. |
| 5,833,673 A | * | 11/1998 | Ockuly ....................... 604/281 |
| 5,957,961 A | * | 9/1999 | Maguire ....................... 607/99 |
| 6,033,403 A | * | 3/2000 | Tu et al. ....................... 606/41 |
| 5,935,124 A | * | 8/2000 | Klumb .......................... 606/42 |
| 6,096,036 A | * | 8/2000 | Bowe ........................... 606/41 |
| 6,123,084 A | * | 9/2000 | Jandak ........................ 128/898 |

OTHER PUBLICATIONS

M. Haissaguerre et al., "Spontaneous Initiation of Atrial Fibrillation by Ectopic Beats Originating in the Pulmonary Veins", The New England Journal of Medicine, 339:659–666 (Sep. 3), 1998.

* cited by examiner

Primary Examiner—Michael Peffley
(74) Attorney, Agent, or Firm—Christie, Parker & Hale, LLP

(57) ABSTRACT

A catheter for ablating tissue comprises a catheter body, a tip section, a branding iron assembly and an infusion tube. The catheter body has an outer wall, proximal and distal ends, and at least one lumen extending therethrough. The tip section comprises a segment of flexible tubing having proximal and distal ends and at least one lumen therethrough. The proximal end of the tip section is fixedly attached to the distal end of the catheter body. The branding iron assembly has proximal and distal ends and is fixedly attached at its proximal end to the distal end of the tubing of the tip section. The branding iron assembly is bent relative to the tubing and comprises a non-retractable tubular electrode formed of a material having shape-memory. The tubular electrode has proximal and distal ends and at least one irrigation port through which fluid can pass from the inside to the outside of the electrode. The infusion tube extends through a lumen in the tip section, with its distal end in fluid communication with the proximal end of the tubular electrode.

32 Claims, 7 Drawing Sheets

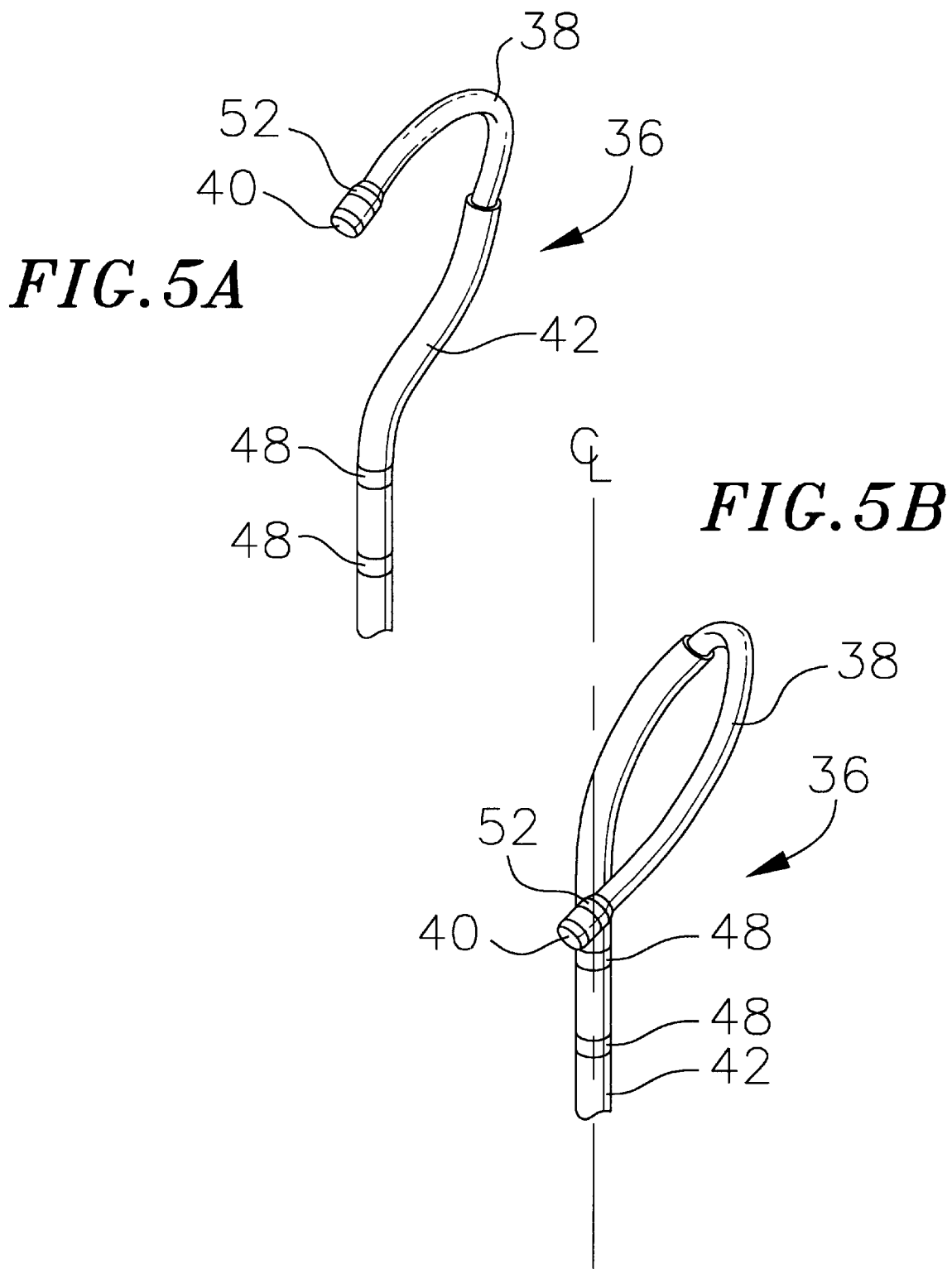

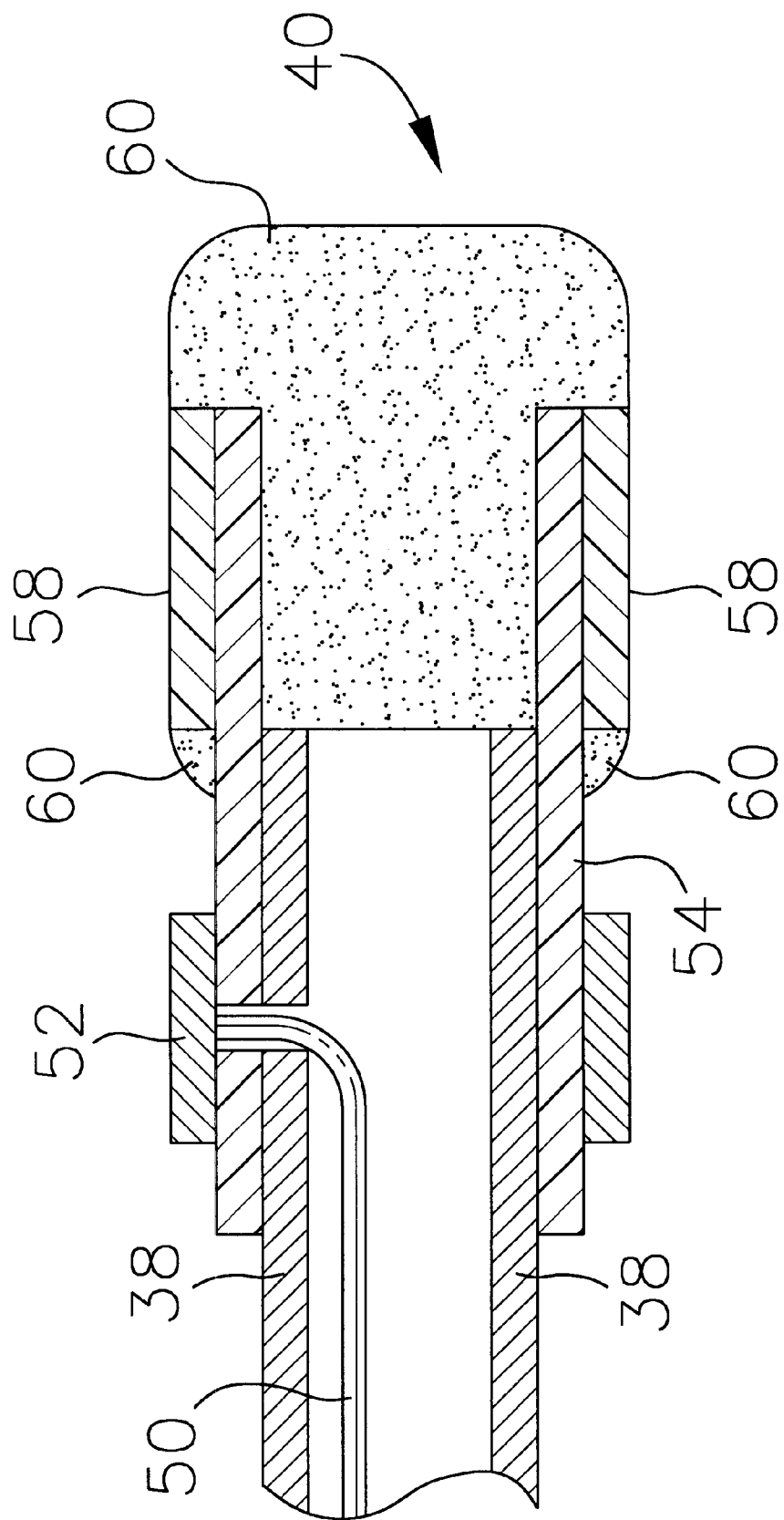

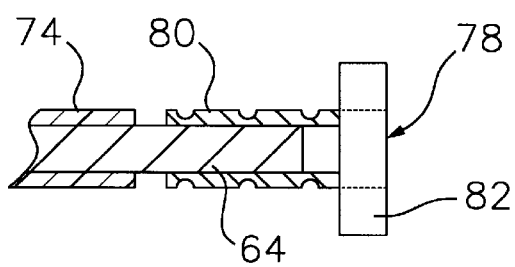
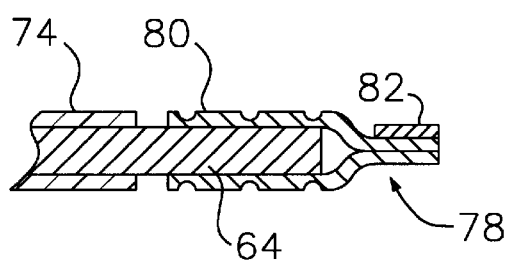
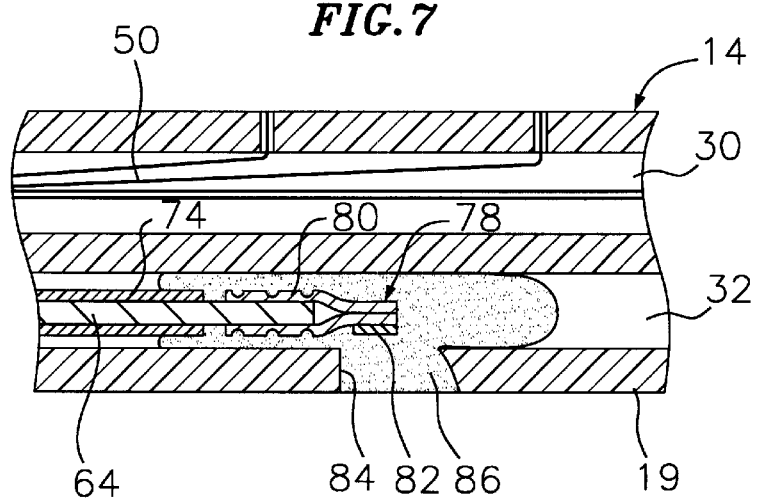

US 6,371,955 B1

ATRIAL BRANDING IRON CATHETER AND A METHOD FOR TREATING ATRIAL FIBRILLATION

FIELD OF THE INVENTION

The present invention relates to an improved steerable electrode catheter having an irrigated tip that is particularly useful for treating atrial fibrillation.

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. It is believed that to treat atrial fibrillation by radio-frequency ablation using a catheter, continuous linear lesions must be formed to segment the heart tissue. By segmenting the heart tissue, no electrical activity can be transmitted from one segment to another. Preferably, the segments are made too small to be able to sustain the fibrillatory process. A preferred technique for treating atrial fibrillation by radio-frequency ablation would be a "branding iron" approach, where a relatively long electrode can be held stationary in good contact with the heart wall while ablation is completed. In this way, a continuous transmural burn may be effected.

U.S. Pat. No. 5,800,428 to Nelson et al. discloses a radio frequency ablation catheter system having a flexible, tubular electrode for creating a continuous linear lesion. The tubular electrode is selectively extendable from the distal end of the catheter. The catheter further comprises mechanisms for remotely manipulating and extending the electrode. However, having an extendable electrode house in the catheter provides less degrees of freedom with respect to the shape, size and length of the tubular electrode. Moreover, the physician has to deal with additional moving and manipulatable parts, adding complexity to the procedure. Further, a retractable electrode can cause contamination because blood or coagulate on the electrode can be pulled into and entrapped inside the catheter. The entrapped coagulate can also affect the ability of the electrode to be further extended and retracted. Accordingly, it would be desirable to provide a catheter design having an electrode for creating linear lesions that overcomes these drawbacks.

SUMMARY OF THE INVENTION

The present invention is directed to a catheter having a non-retractable "branding iron" electrode. In one embodiment, the invention is directed to a catheter for ablating tissue comprising a catheter body, a tip section, a branding iron assembly, and a means for introducing fluid into the tubular electrode. The catheter body has an outer wall, proximal and distal ends, and at least one lumen extending therethrough. The tip section comprises a segment of flexible tubing having proximal and distal ends and at least one lumen therethrough. The proximal end of the tip section is fixedly attached to the distal end of the catheter body. The branding iron assembly has proximal and distal ends and is fixedly attached at its proximal end to the distal end of the tubing of the tip section. The branding iron assembly is bent relative to the tubing and comprises a non-retractable tubular electrode formed of a material having shape-memory having at least one irrigation port through which fluid can pass from the inside to the outside of the electrode. A preferred means for introducing fluid comprises an infusion tube extending through a lumen in the tip section and having proximal and distal ends. The distal end of the infusion tube is in fluid communication with the proximal end of the tubular electrode. The tubular electrode of the invention acts as a branding iron, forcing tissue out of shape. This design produces more pressure on the tissue than a traditional catheter tip comprising a flexible plastic tubing with a series of ring electrodes mounted thereon.

In another embodiment, the invention is directed to a method for treating atrial fibrillation. According to the method, the distal end of a catheter as described above is inserted into an atria of the heart. At least one linear lesion is then formed in the atrial tissue with the tubular electrode.

In another embodiment, the invention is directed to a method for treating atrial fibrillation comprising providing a catheter as described above and a guiding sheath having proximal and distal ends. The guiding sheath is introduced into the body so that the distal end of the guiding sheath is in an atria of the heart. The catheter is then inserted into the proximal end of the guiding sheath and fed through the guiding sheath so that the distal end of the catheter extends out the distal end of the guiding sheath. At least one linear lesion is then formed in the atrial tissue with the tubular electrode.

In still another embodiment, the invention is directed to a method for treating atrial fibrillation similar to as described above. The catheter comprises a branding iron assembly that is generally L-shaped. The at least one linear lesion is formed in an open region of the heart with the tubular electrode.

In yet another embodiment, the invention is directed to a method for treating atrial fibrillation similar to as described above. The catheter comprises a branding iron assembly that is generally lasso-shaped. The at least one linear lesion is formed in or around a blood vessel with the tubular electrode.

In still yet another embodiment, the invention is directed to a method for treating atrial fibrillation similar to as described above. The branding iron assembly further includes an atraumatic tip comprising a coil spring, which is mounted at the distal end of the assembly.

DESCRIPTION OF THE DRAWINGS

These and other features and advantages of the present invention will be better understood by reference to the following detailed description when considered in conjunction with the accompanying drawings wherein:

FIGS. 5A and 5B are perspective views of an alternate branding iron electrode assembly according to the invention.

FIG. 6 is a side cross-sectional view of the distal end of an alternate branding iron electrode assembly according to the invention.

FIG. 7 is a cross sectional view of a portion of the catheter tip section showing one means for attaching the puller wire.

FIG. 8 is a top cross sectional views of a preferred puller wire anchor.

FIG. 9 is a side cross sectional views of the puller wire anchor of FIG. 8.

DETAILED DESCRIPTION

Figure 1:
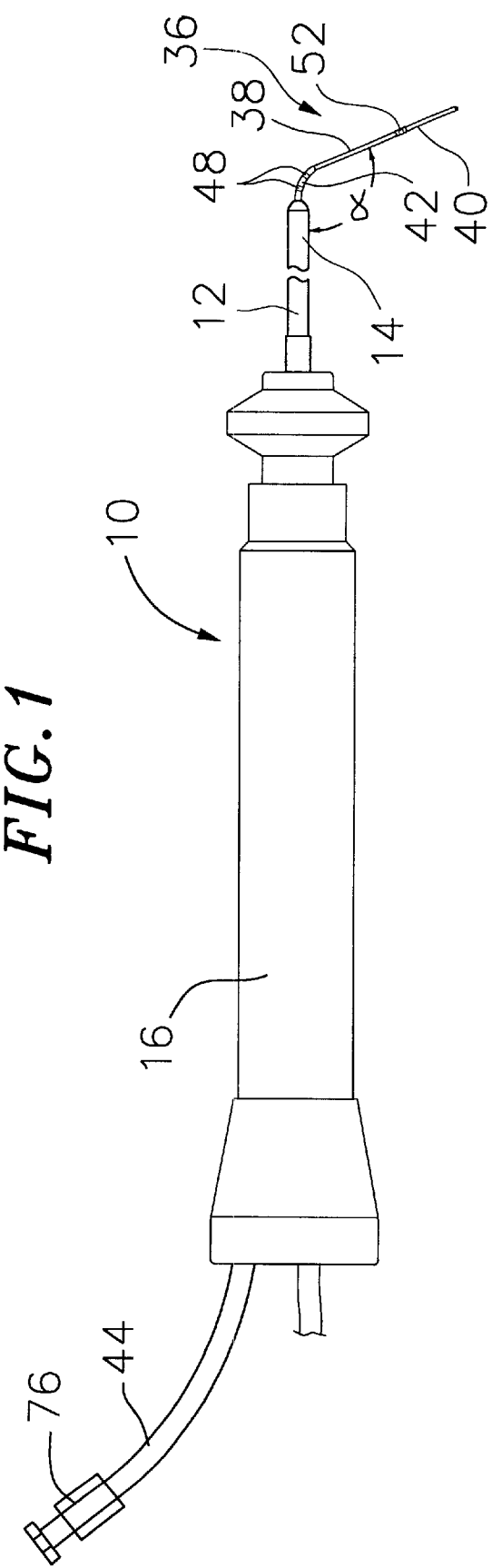
FIG. 1 is a side cross-sectional view of an embodiment of the catheter of the invention.

In a particularly preferred embodiment of the invention, there is provided a steerable catheter having an irrigated branding iron electrode. As shown in FIG. 1, catheter 10 comprises an elongated catheter body 12 having proximal and distal ends, a tip section 14 at the distal end of the catheter body, and a control handle 16 at the proximal end of the catheter body.

Figure 2:
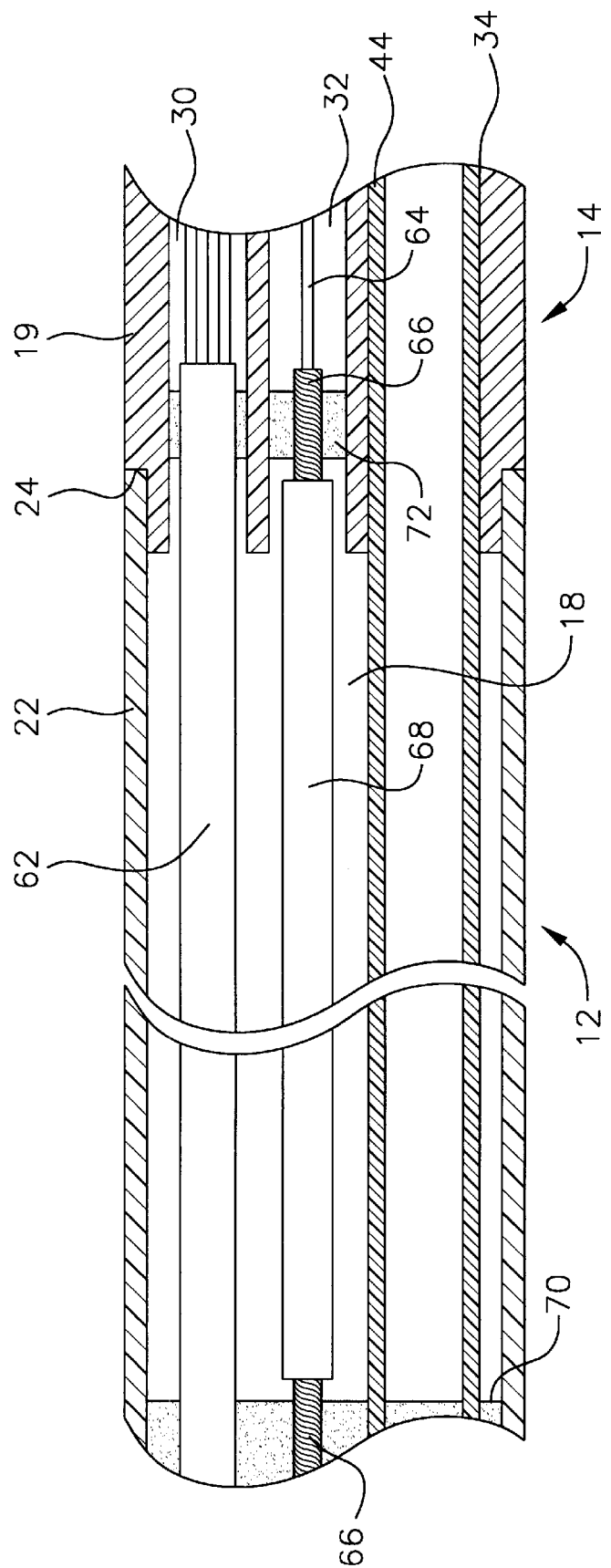
FIG. 2 is a side cross-sectional view of a catheter body according to the invention, including the junction between the catheter body and tip section.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of polyurethane or PEBAX. The outer wall 22 comprises an imbedded braided mesh of stainless steel or the like to increase torsional stiffness of the catheter body 12 so that, when the control handle 16 is rotated, the tip section 14 of the catheter 10 will rotate in a corresponding manner.

The outer diameter of the catheter body 12 is not critical, but is preferably no more than about 8 french, more preferably 7 french. Likewise the thickness of the outer wall 22 is not critical, but is thin enough so that the central lumen 18 can accommodate an infusion tube, a puller wire, lead wires, and any other wires, cables or tubes. If desired, the inner surface of the outer wall 22 is lined with a stiffening tube (not shown) to provide improved torsional stability. A particularly preferred catheter has an outer wall 22 with an outer diameter of from about 0.090 inch to about 0.94 inch and an inner diameter of from about 0.061 inch to about 0.065 inch.

The tip section 14 comprises a short section of tubing 19 having three lumens. The first lumen 30 electrode carries lead wires 50, the second lumen 32 carries a puller wire, and the third lumen 34 carries an infusion tube. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like. The size of the lumens is not critical. In a particularly preferred embodiment, the tip section 14 has an outer diameter of about 7 french (0.092 inch) and the first lumen 30 and second lumen 32 are generally about the same size, each having a diameter of from about 0.020 inch to about 0.024 inch, preferably 0.022 inch, with the third lumen 34 having a slightly larger diameter of from about 0.032 inch to about 0.038 inch, preferably 0.035 inch.

A preferred means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by glue or the like.

If desired, a spacer (not shown) can be located within the catheter body between the distal end of the stiffening tube and the proximal end of the tip section. The spacer provides a transition in flexibility at the junction of the catheter body and tip section, which allows this junction to bend smoothly without folding or kinking. A catheter having such a spacer is described in U.S. patent application Ser. No. 08/924,616, entitled "Steerable Direct Myocardial Revascularization Catheter", the disclosure of which is incorporated herein by reference.

Figure 3:
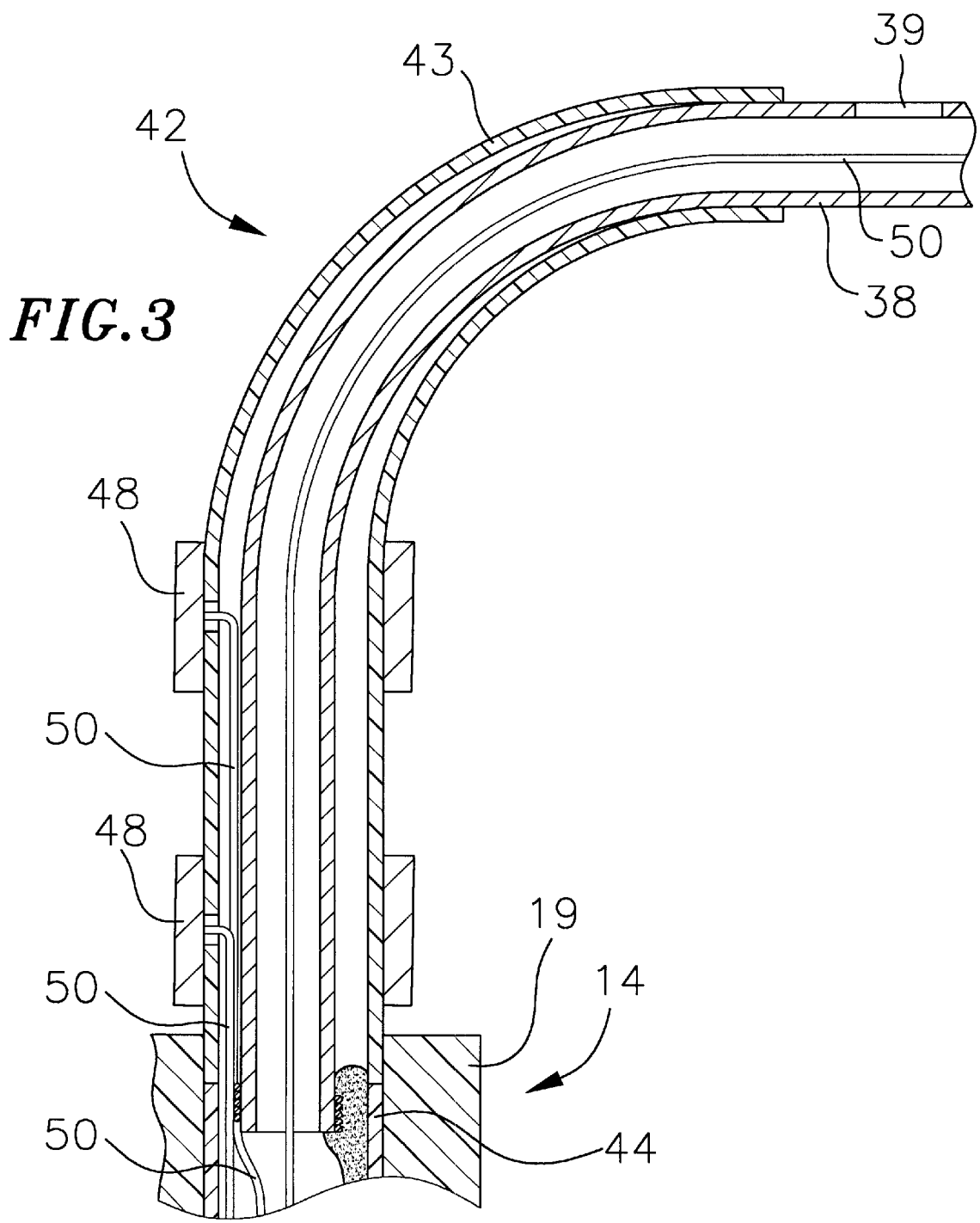
FIG. 3 is a side cross-sectional view of the proximal end of a branding iron electrode assembly according to the invention.
Figure 4:
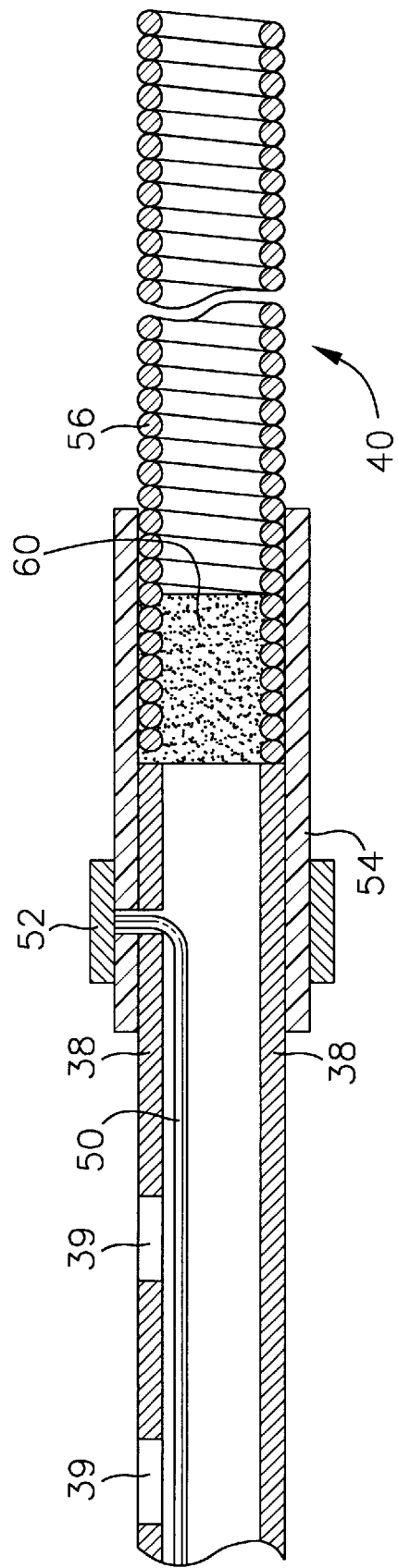
FIG. 4 is a side cross-sectional view of the distal end of the branding iron electrode assembly of FIG. 3.

At the distal end of the tip section 14 is a non-retractable branding iron electrode assembly 36, as shown in FIGS. 1, 3 and 4. The branding iron electrode assembly 36 has proximal and distal ends and comprises a tubular electrode 38, an atraumatic tip 40 at the distal end of the assembly, and a non-conductive segment 42 at the proximal end of the assembly. The tubular electrode 38, which has proximal and distal ends, is made of a material having shape-memory, i.e., that can be straightened or bent out of its original shape upon exertion of a force and is capable of substantially returning to its original shape upon removal of the force. A particularly preferred material for the tubular electrode 38 is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. A particularly preferred material is nitinol form from 50.8 atomic % nickel, with the balance titanium, having an austenite finish and a transition temperature from about +5° C. to about −25° C., which is commercially available from Nitinol Device Corp. (Fremont, Calif.). Preferably the tubular electrode 38 has an inner diameter of about 0.020 inch and an outer diameter of about 0.026 inch. The length of the exposed portion of the tubular electrode 38 can vary depending on the desired length of the lesion to be created, and preferably ranges from about 8 mm to about 2 cm, more preferably from about 1.2 cm to about 1.6 cm, to create a relatively long lesion.

An electrode lead wire 50 is attached to the tubular electrode 38 for electrical connection to a suitable connector (not shown), which is attached to a source of RF energy (not shown). The electrode lead wire 50 is wrapped around the proximal end of the tubular electrode 38.

The branding iron assembly 36 is shaped so that it is bent relative to the straight tubing 19 of the tip section 14. As used herein, the term "bent" when used to describe the branding iron assembly 36 is intended to mean that the assembly is curved, bent or angled to any extent at any point along its length. With this design, when a physician deflects the tip section 14, the tubular electrode 38 is pressed against the tissue, creating a "branding iron" effect. In contrast, a physician using a straight catheter having one or more electrodes along the length of its distal end to create a linear lesion will find it difficult to provide the same amount of pressure on the tissue with the electrode(s). The particular shape of the branding iron assembly 36 depends on the desired application, i.e., the precise location in the atrium in which the catheter is to be used, and for example, can be bent in a single plane or in multiple planes.

In one embodiment, as shown in FIG. 1, the branding iron assembly 36 is generally L-shaped and lies in a single plane. The proximal end of the assembly 36 is generally straight and collinear with the tubing 19 of the tip section 14. The assembly 36 bends at a point along its length. Preferably the straight proximal end of the assembly 36 is sufficiently long to mount one or more mapping ring electrodes, as described in more detail below. After the bend, the distal end of the assembly 36 is generally straight, so that the exposed portion of the tubular electrode 38 is generally straight. The atraumatic tip 40 is generally collinear with the tubular electrode 38. The branding iron assembly 36 of this embodiment is preferably shaped so that it forms an angle α ranging from about 60 degrees to about 140 degrees. This design is particularly useful for ablation in the open region of the heart.

In an alternative embodiment, shown in FIGS. 5A and 5B, the branding iron assembly 36 is generally lasso-shaped. The proximal end of the assembly 36 is generally collinear with the tubing 19 of the tip section 14. The assembly 36 curves at its distal end to form a slanted semi-circle, i.e., lying in more than one plane, as best shown in FIG. 5B. In this embodiment, the tubular electrode 38 is generally curved. This design is particularly useful for ablation in or around a blood vessel, such as the pulmonary vein. As would be recognized by one skilled in the art, other shapes can be provided for the electrode assembly 36. For example, in the embodiment of FIG. 5B, the tubular electrode 38 could form a full circle The tubular electrode 3;8 contains a series of irrigation ports 39 through which fluid can pass during an ablation procedure. Preferably the irrigation ports 39 are located only on the side of the tubular electrode 38 that is to be in contact with the tissue to be ablated. The irrigation ports 39 can be any suitable shape, such as rectangular or oval slots or round holes. Preferably, in the embodiment shown in FIGS. 1, 3 and 4, the tubular electrode 38 has six irrigation ports 39, each forming a slot or ellipse with a length of about 0.020 inch. Preferably the irrigation ports 39 are spaced apart from each other a distance of about 0.125 inch. Having a limited number of irrigation ports 39 on the side of the tubular electrode 38 in contact with the tissue to be ablated allows for more even fluid flow out of the electrode.

The non-conductive segment 42 of the branding iron assembly 36 comprises a non-conductive covering 43, e.g. polyimide, extending over the proximal end of the tubular electrode 38. Two proximal mapping ring electrodes 48 are mounted on the non-conductive covering 43. The proximal mapping ring electrodes 48 can be made of any suitable material, and are preferably made of platinum or platinum and iridium. Each ring electrode 48 can be mounted by any suitable technique, and is preferably mounted by first forming a hole in the non-conductive covering 43. An electrode lead wire 50 is fed through the hole, and the ring electrode 48 is welded in place over the lead wire and non-conductive covering 43. The lead wires 50 extend between the non-conductive covering 43 and the tubular electrode 38.

A distal mapping electrode 52 is mounted near the distal end of the tubular electrode 38. A non-conductive sleeve 54, e.g., made of polyimide, is placed between the tubular electrode 38 and the distal mapping electrode 52. The distal mapping electrode 5 electrically attached to an electrode lead wire 50 in a manner similar to that described above, although the lead wire, which has a non-conductive coating, extends through the interior of the tubular electrode 38. The presence and number of mapping electrodes can vary as desired.

The non-conductive sleeve 54 extends beyond the distal end of the tubular electrode 38 an over the junction of the tubular electrode 38 and the atraumatic tip 40. The atraumatic tip 40 can be of any suitable design that prevents the distal end of the tubular electrode 38 from penetrating tissue. In the depicted embodiment, the atraumatic tip 40 is formed of a tightly wound coil spring 56 made, for example, of stainless steel, such as the mini guidewire commercially available from Cordis Corporation (Miami, Fla.). The proximal end of the coil spring 56 is mounted in the distal end of the non-conductive sleeve 54 polyurethane glue or the like. The polyurethane glue also acts to seal the distal end of the tubular electrode 38 so that any irrigation fluid, discussed in more detail below, cannot flow out the distal end of the electrode. In the depicted embodiment, the atraumatic tip 40 has a length of about 0.50 inch, but can be any desired length, for example, ranging from about 0.25 inch to about 1.0 inch. The atraumatic tip 40 is preferably sufficiently long to serve as an anchor for introducing the catheter into a guiding sheath, as discussed in more detail below, particularly when the tubular electrode is curved and must be straightened upon introduction into the sheath. Without having the atraumatic tip as an anchor, the tubular electrode has a tendency to pull out of the guiding sheath upon its introduction into the guiding sheath. Additionally, if desired, the atraumatic tip 40 can be formed, at least in part, of a radiopaque material to aid in the positioning of the tubular electrode 38 under fluoroscopy.

The atraumatic tip 40 can be of any suitable design that protects the tubular electrode 38 from puncturing the heart tissue. For example, an alternative design of an atraumatic tip 40, as shown in FIG. 6, is in the form of a ball. To form the ball, the distal end of the non-conductive sleeve 54 is covered with a short length of thick non-conductive tubing 58, made of polyimide, polyurethane or the like. Polyurethane adhesive 60 or the like is applied into and around the edges of the non-conductive tubing 58 to round off the edges of the distal end of the tip 40.

The lead wires 50 attached to the tubular electrode 38 and ring electrodes 48 extend through the first lumen 30 of tip section 14, the central lumen 18 of the catheter body 12, and the control handle 16, and terminate at their proximal end in an input jack (not shown) that may be plugged into an appropriate monitor (not shown). The portion of the lead wires 50 extending through the central lumen 18 of the catheter body 12, control handle 16 and proximal end of the tip section 14 are enclosed within a protective sheath 62, which can be made of any suitable material, preferably polyimide. The protective sheath 62 is anchored at its distal end to the proximal end of the tip section 14 by gluing it in the first lumen 30 with polyurethane glue or the like.

If desired, a temperature sensing means (not shown) can be provided for the tubular electrode 38. Any conventional temperature sensing means, e.g., a thermocouple or thermistor, may be used. One preferred temperature sensing means comprises a thermocouple formed by a wire pair. One wire of the wire pair is a copper wire, e.g., a number 38 copper wire. The other wire of the wire pair is a constant an wire, which gives support and strength to the wire pair. The wires and can extend through the first lumen 30 in the tip section along with the lead wires 50. Within the catheter body 12 the wires and can extend through the protective sheath 39, also with the lead wires 50. The wires and then extend out through the control handle 16 and to a connector (not shown) connectable to a temperature monitor (not shown). Alternatively, the temperature sensing means may be a thermistor. A suitable thermistor for use in the present invention is Model No. AB6N2-GC14KA143E/37C sold by Thermometrics (New Jersey).

A puller wire 64 is provided for deflection of the tip section 14. The puller wire 64 extends through the catheter body 12, is anchored at its proximal end to the control handle 16, and is anchored at its distal end to the tip section 14. The puller wire 64 is made of any suitable metal, such as stainless steel or Nitinol, and is preferably coated with Teflon® or the like. The coating imparts lubricity to the puller wire 64. The puller wire 64 p ably has a diameter ranging from about 0.006 to about 0.010 inch.

A compression coil 66 is situated within the catheter body 12 in surrounding relation to the puller 64. The compression coil 66 extends from the proximal end of the catheter body 12 to the proximal end of the tip section 14. The compression coil 66 is made of any suitable metal, preferably stainless steel. The compression coil 66 is tightly wound on itself to provide flexibility, i.e., bending, but to resist compression. The inner diameter of the compression coil 66 is preferably slightly larger than the diameter of the puller wire 64. The Teflon® coating on the puller wire 64 allows it to slide freely within the compression coil 66. If desired, particularly if the lead wires 50 are not enclosed by a protective sheath 62, he outer surface of the compression coil 66 is covered by a flexible, non-conductive sheath 68, e.g., made of polyimide tubing, to prevent contact between the compression coil and any other wires within the catheter body 12.

The compression coil 66 is anchored at its proximal end to the outer wall 22 of the catheter body 12 by proximal glue joint 70 and at its distal end to the tip section 14 by distal glue joint 72. Both glue joints 70 and 72 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 which is heated sufficiently to form a permanent hole. The glue is then introduced through the hole to the outer surface of the compression coil 66 and wicks around the outer circumference to form a glue joint about the entire circumference of the compression coil 66.

The puller wire 64 extends into the second lumen 32 of the tip section 14. Preferably the puller wire 64 is anchored at its distal end to the side of the tip section 14, as shown in FIGS. 7 to 9. A T-shaped anchor 78 is formed which comprises a short piece of tubular stainless steel 80, e.g., hypodermic stock, which is fitted over the distal end of the puller wire 64 and crimped to fixedly secure it to the puller wire. The distal end of the tubular stainless steel 80 is fixedly attached, e.g., by welding, to a stainless steel cross-piece 82 such as stainless steel ribbon or the like. The cross-piece 82 sits in a notch 84 in a wall of the flexible tubing 19 that extends into the second lumen 32 of the tip section 14. The stainless steel cross-piece 82 is larger than the opening and, therefore, cannot be pulled through the opening. The portion of the notch 84 not filled by the cross-piece 82 is filled with glue 86 or the like, preferably a polyurethane glue, which is harder than the material of the flexible tubing 19. Rough edges, if any, of the cross-piece 82 are polished to provide a smooth, continuous surface with the outer surface of the flexible tubing 19. Within the second lumen 32 of the tip section 14, the puller wire 64 extends through a plastic, preferably Teflon®, puller wire sheath 74, which prevents the puller wire 64 from cutting into the wall of the tip section 14 when the tip section is deflected. Any other suitable technique for anchoring the puller wire 64 in the tip section 14 can also be used.

Longitudinal movement of the puller wire 42 relative to the catheter body 12, which results in deflection of the tip section 14 is accomplished by suitable manipulation of the control handle 16. Examples of suitable control handles for use in the present invention are disclosed, for example, in U.S. Pat. Nos. Re 34,502 and 5,897,529, the entire disclosures of which are incorporated herein by reference.

Within the third lumen 34 of the tip section 14 is provided an infusion tube 44 for infusing fluids, e.g., saline, to cool the tubular electrode 38. The infusion tube 44 extends through the third lumen 34 of the tip section 14, through the catheter body 12, out the proximal end of the control handle 16, and terminates in a luer hub 76 or the like at a location proximal to the control handle. In an alternative arrangement, a single lumen side arm (not shown) is fluidly connected to the central lumen 18 near the proximal end of the catheter body 12, as described in more detail in U.S. Pat. No. 6,120,476, the entire disclosure of which is incorporated herein by reference. Alternatively, the infusion tube 44 can terminate within the distal end of the third lumen 34 of the tip section 14, with a second infusion tube provided that extends from the proximal end of the third lumen, through the catheter body 12 and out through the control handle 16. Such a design is also described in more detail in U.S. Pat. No. 6,120,476. As shown in FIG. 3, the distal end of the infusion tube 44 extends over the proximal end of the tubular electrode 38, including the lead wire 50 wrapped around the tubular electrode. The infusion tube 44 is attached to the tubular electrode 38 with polyurethane glue or the like, which also acts to seal the third lumen 34 so that fluids cannot pass into or out of the third lumen other than through the infusion tube and tubular electrode.

In use, a suitable guiding sheath is inserted into the patient. An example of a suitable guiding sheath for use in connection with the present invention is the Preface™ Braiding Guiding Sheath, commercially available from Cordis Webster (Diamond Bar, Calif.). The distal end of the sheath is guided into one of the atria. A catheter in accordance with the present invention is fed through the guiding sheath until its distal end extends out of the distal end of the guiding sheath. As the catheter is fed through the guiding sheath, the tubular electrode 38 can be straightened to fit through the sheath, and it will return to its original shape upon removal of the sheath.

The tubular electrode 38 is then used to form continuous linear lesions by ablation. As used herein, a linear lesion refers to any lesion, whether curved or straight, between two anatomical structures in the heart that is sufficient to block a wavelet, i.e., forms a boundary for the wavelet. Anatomical structures, referred to as "atrial trigger spots", are those regions in the heart having limited or no electrical conductivity and are described in Haissaguerre et al., "Spontaneous Initiation of Atrial Fibrillation by Ectopic Beats Originating in the Pulmonary Veins", New England Journal of Medicine, 339:659–666 (Sep. 3, 1998), the disclosure of which is incorporated herein by reference. The linear lesions typically have a length of from about 1 cm to about 4 cm, but can be longer or shorter as necessary for a particular procedure.

If desired, two or more puller wires can be provided to enhance the ability to manipulate the tip section. In such an embodiment, a second puller wire and a surrounding second compression coil extend through the catheter body and into an additional off-axis lumen in the tip section. The first puller wire is preferably anchored proximal to the anchor location of the second puller wire. Suitable designs of catheters having two or more puller wires, including suitable control handles for such embodiments, are described, for example, in U.S. Pat. Nos. 6,123,699, 6,171,277, and 6,183, 463, and allowed U.S. Patent Application Ser. No. 09/157, 055, filed Sep. 18, 1998, the disclosures of which are incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter for ablating tissue, the catheter comprising:
   a catheter body having an outer wall, proximal and distal ends, and at least one lumen extending therethrough;
   a tip section comprising a segment of flexible tubing having proximal and distal ends and at least one lumen therethrough, the proximal end of the tip section being fixedly attached to the distal end of the catheter body;
   a branding iron assembly having proximal and distal ends fixedly attached at its proximal end to the distal end of the tubing of the tip section and bent relative to the tubing, the branding iron assembly comprising a non-retractable tubular electrode formed of a material having shape-memory having at least one irrigation port through which fluid can pass from the inside to the outside of the electrode; and
   means for introducing fluid into the tubular electrode.

2. A catheter according to claim 1, wherein the introducing means comprising an infusion tube extending through a lumen in the tip section and having proximal and distal ends, wherein the distal end of the infusion tube is in fluid communication with the proximal end of the tubular electrode.

3. A catheter according to claim 1, wherein the branding iron assembly has a shape that is bent relative to the tubing at room temperature.

4. A catheter for ablating tissue, the catheter comprising:
   a catheter body having an outer wall, proximal and distal ends, and at least one lumen extending therethrough;
   a tip section comprising a segment of flexible tubing having proximal and distal ends and at least one lumen therethrough, the proximal end of the tip section being fixedly attached to the distal end of the catheter body;
   a branding iron assembly having proximal and distal ends fixedly attached at its proximal end to the distal end of the tubing of the tip section and bent relative to the tubing, the branding iron assembly comprising a non-retractable tubular electrode formed of a material having shape-memory having proximal and distal ends and at least one irrigation port through which fluid can pass from the inside to the outside of the electrode; and
   an infusion tube extending through a lumen in the tip section and having proximal and distal ends, wherein the distal end of the infusion tube is in fluid communication with the proximal end of the tubular electrode.

5. A catheter according to claim 4, wherein the branding iron assembly is generally L-shaped.

6. A catheter according to claim 4, wherein the branding iron assembly is generally lasso-shaped.

7. A catheter according to claim 4, wherein the tubular electrode is made of a nickel/titanium alloy.

8. A catheter according to claim 4, wherein the tubular electrode is made of nitinol.

9. A catheter according to claim 4, wherein the tubular electrode has an exposed portion having a length ranging from about 8 mm to about 2 cm.

10. A catheter according to claim 9, wherein the exposed portion of the tubular electrode has a length ranging from about 1.2 cm to about 1.6 cm.

11. A catheter according to claim 9, wherein the exposed portion of the tubular electrode is generally straight.

12. A catheter according to claim 4, wherein the distal end of the tubular electrode extends into the lumen in the tip section into which the infusion tube extends.

13. A catheter according to claim 12, wherein the branding iron assembly further comprises a non-conductive covering over the proximal end of the tubular electrode.

14. A catheter according to claim 13, wherein the branding iron assembly further comprises at least one mapping electrode mounted on the non-conductive covering.

15. A catheter according to claim 4, wherein the branding iron assembly further comprises at least one mapping electrode mounted on the assembly distal the tubular electrode.

16. A catheter according to claim 4, wherein the at least one irrigation port is located only on the side of the tubular electrode that is to be in contact with the tissue to be ablated.

17. A catheter according to claim 4, wherein the branding iron assembly further comprises an atraumatic tip at its distal end.

18. A catheter according to claim 17, wherein the atraumatic tip comprises a coil spring.

19. A catheter according to claim 17, wherein the atraumatic tip has a length ranging from about 0.25 inch to about 1.0 inch.

20. A catheter according to claim 4, further comprising a control handle mounted at the proximal end of the catheter body and means for deflecting the tip section by manipulation of the control handle.

21. A catheter according to claim 20, wherein the control handle comprises a first member fixedly attached to the proximal end of the catheter body and a second member that is movable relative to the first member.

22. A catheter according to claim 21, wherein the deflecting means comprises a puller wire having a proximal end and a distal end, the puller wire extending from the control handle, through the catheter body and into the a lumen in the tip section, wherein the distal end of the puller wire is fixedly secured within the tip section and the proximal end of the puller wire is fixedly secured to the second member of the control handle, whereby manipulation of the first member of the control handle relative to the second member of the control handle moves the puller wire relative to the catheter body, resulting in deflection of the tip section.

23. A catheter according to claim 4, wherein the branding iron assembly has a shape that is bent relative to the tubing at room temperature.

24. A method for treating atrial fibrillation comprising:
   inserting the distal end of a catheter according to claim 4 into an atria of the heart; and
   forming at least one linear lesion in the atrial tissue with the tubular electrode.

25. A method for treating atrial fibrillation comprising:
   providing a catheter as recited in claim 4 and a guiding sheath having proximal and distal ends;
   inserting the guiding sheath into the body so that the distal end of the guiding sheath is in an atria of the heart;
   inserting the catheter into the proximal end of the guiding sheath and feeding the catheter through the guiding sheath so that the distal end of the catheter extends out the distal end of the guiding sheath; and
   forming at least one linear lesion in the atrial tissue with the tubular electrode.

26. A method according to claim 25, wherein the at least one linear lesion has a length ranging from about 1 cm to about 4 cm.

27. A method for treating atrial fibrillation comprising:
   providing a catheter as recited in claim 5 and a guiding sheath having proximal and distal ends;
   inserting the guiding sheath into the body so that the distal end of the guiding sheath is in an atria of the heart;

inserting the catheter into the proximal end of the guiding sheath and feeding the catheter through the guiding sheath so that the distal end of the catheter extends out the distal end of the guiding sheath; and forming at least one linear lesion in the atrial tissue in an open region of the heart with the tubular electrode.

28. A method according to claim 27, wherein the at least one linear lesion has a length ranging from about 1 cm to about 4 cm.

29. A method for treating atrial fibrillation comprising:

providing a catheter as recited in claim 5 and a guiding sheath having proximal and distal ends;

inserting the guiding sheath into the body so that the distal end of the guiding sheath is in an atria of the heart;

inserting the catheter into the proximal end of the guiding sheath and feeding the catheter through the guiding sheath so that the distal end of the catheter extends out the distal end of the guiding sheath; and forming at least one linear lesion in or around a blood vessel with the tubular electrode.

30. A method according to claim 29, wherein the at least one linear lesion has a length ranging from about 1 cm to about 4 cm.

31. A method for treating atrial fibrillation comprising:

providing a catheter as recited in claim 18 and a guiding sheath having proximal and distal ends;

inserting the guiding sheath into the body so that the distal end of the guiding sheath is in an atria of the heart;

inserting the catheter into the proximal end of the guiding sheath and feeding the catheter through the guiding sheath so that the distal end of the catheter extends out the distal end of the guiding sheath;

deflecting the tip section of the catheter so that the tubular electrode is pressed against atrial tissue; and forming at least one linear lesion in the atrial tissue with the tubular electrode.

32. A method according to claim 31, wherein the at least one linear lesion has a length ranging from about 1 cm to about 4 cm.

* * * * *